United States Patent [19]

Hedberg

[11] Patent Number: 5,441,521
[45] Date of Patent: Aug. 15, 1995

[54] HEART DEFIBRILLATOR

[75] Inventor: Sven-Erik Hedberg, Kungsaengen, Sweden

[73] Assignee: Pacesetter AB, Solna, Sweden

[21] Appl. No.: 114,825

[22] Filed: Sep. 2, 1993

[30] Foreign Application Priority Data

Sep. 16, 1992 [SE] Sweden ................... 9202663

[51] Int. Cl.⁶ ......................................... A61N 1/39
[52] U.S. Cl. ............................................... 607/6
[58] Field of Search ........................... 607/5, 6, 8

[56] References Cited

U.S. PATENT DOCUMENTS

| | | |
|---|---|---|
| 4,407,288 | 10/1983 | Langer et al. . |
| 4,559,946 | 12/1985 | Mower . |
| 4,637,397 | 1/1987 | Jones et al. . |
| 4,693,253 | 9/1987 | Adams . |
| 4,785,812 | 11/1988 | Pihl et al. ................ 607/8 |
| 4,800,883 | 1/1989 | Winstrom . |
| 4,821,723 | 4/1989 | Baker, Jr. et al. . |
| 4,850,357 | 7/1989 | Bach, Jr. . |
| 4,940,054 | 7/1990 | Grevis et al. . |
| 4,998,531 | 3/1991 | Bocchi et al. . |
| 5,107,834 | 4/1992 | Ideker et al. . |
| 5,111,813 | 5/1992 | Charbonnier et al. . |
| 5,314,448 | 5/1994 | Kroll et al. ................ 607/5 |

FOREIGN PATENT DOCUMENTS 0263505  1/1988  European Pat. Off. .

OTHER PUBLICATIONS

"Implantable Cardioverters and Defibrillators Current Problems in Cardiology," Troup, Year Book Medical Publishers, Inc. vol. XIV, No. 12, Dec., 1989, pp. 699ff.

Primary Examiner—William E. Kamm
Assistant Examiner—Scott M. Getzow
Attorney, Agent, or Firm—Hill, Steadman & Simpson

[57] ABSTRACT

A heart defibrillator includes a defibrillation circuit for delivering defibrillation pulses. The defibrillation circuit also emits a pre-pulse before the defibrillation pulse. The pre-pulse is not as intense as the defibrillation pulse, but is still intense enough to induce mechanical contraction of muscles in parts of the thorax and possibly the heart.

12 Claims, 2 Drawing Sheets

HEART DEFIBRILLATOR

BACKGROUND OF THE INVENTION

1. Field of the Invention

The present invention relates to a heart defibrillator for delivering defibrillation pulses.

2. Description of the Prior Art

Complete therapeutic devices for stimulating the heart have previously been disclosed in, e.g., U.S. Pat. No. 4,407,288 and European Application 0 253 505. These devices are devised to emit electrical impulses of varying strength and frequency for various pacemaker functions, cardioversion or heart defibrillation.

SUMMARY OF THE INVENTION

An object of the present invention is to produce a heart defibrillator making possible effective heart defibrillation with the expenditure of less energy than has hitherto been possible.

The above object is achieved in accordance with the principles of the present invention in a heart defibrillator wherein a pre-pulse is generated prior to the generation of the actual pulse which effects defibrillation. The pre-pulse has a lower energy content than the pulse which effect defibrillation.

When a pre-pulse, not as intense as a conventional defibrillation pulse but still intense enough to induce mechanical contraction of muscles in parts of the thorax and possibly the heart, is emitted before the actual defibrillation pulse, the heart and the thorax are geometrically affected, and the heart's electrical conductivity should change, thereby enhancing the effect of the subsequent defibrillation pulse. The pre-pulse achieves mechanical preparation of the heart before the defibrillation pulse is emitted.

According to embodiments of the defibrillator of the invention, the pre-pulse and the defibrillation pulse can be emitted between the same or different electrodes, the electrodes being selected for the pulses such that the current distribution and the current density in myocardium is optimal for the defibrillation pulse. The time at which the defibrillation pulse is emitted after the pre-pulse is selected so an optimal effect is achieved, either by determining the time on the basis of practical experience or automatically with the aid of an impedance measurement circuit which measures the impedance between the defibrillation electrodes after the pre-pulse and which controls the defibrillation circuitry so the defibrillation pulse is emitted when the impedance reaches a specific, optimal value. This optimal impedance condition is an impedance situation at which successful defibrillation from experience is known to be most likely.

According to another embodiment of the defibrillator of the invention, the impedance measurement circuit is arranged to control the defibrillation circuit so that a defibrillation pulse is emitted when the impedance between the defibrillation electrodes has dropped to a designated value.

DESCRIPTION OF THE PREFERRED EMBODIMENTS

Figure 1:
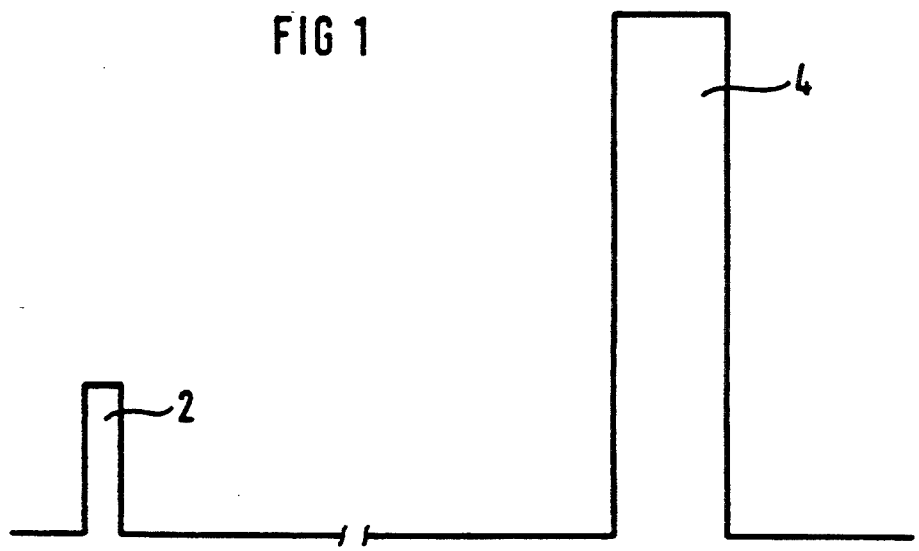
FIG. 1 shows an example of a pre-pulse and a defibrillation pulse emitted by a heart defibrillator according to the invention.
Figure 2:
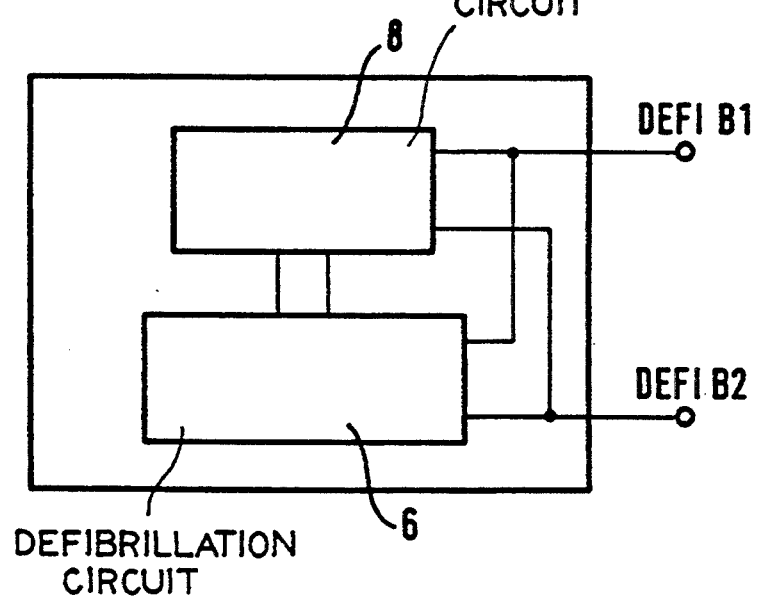
FIG. 2 shows the general structure, in block diagram form, of a heart defibrillator according to the invention.

FIG. 1 shows a pre-pulse 2 which is emitted by the heart defibrillator according to the invention before the actual defibrillation pulse 4. The pre-pulse is strong enough to induce mechanical contraction of the muscles in parts of the thorax and the heart. Thus, tissue in the heart contracts, achieving a kind of mechanical preparation of the heart, thereby improving likelihood of the subsequent defibrillation pulse attaining the desired defibrillation of the heart.

The energy of the pre-pulse 2 is accordingly much less than the energy in the defibrillation pulse 4. Since the heart is prepared by the pre-pulse 2, the energy of the subsequent defibrillation pulse 4 can be reduced, compared to defibrillation pulses generated by known defibrillators, while still reliably producing effective defibrillation of the heart. Thus, effective heart defibrillation with the expenditure of less total energy is possible with a defibrillator according to the invention.

The defibrillator according to the invention includes a defibrillation circuit 6 which emits pre-pulses 2 and defibrillation pulses 4 across electrode contacts DEFIB 1 and DEFIB 2. The defibrillation circuit 6 contains a control unit in the form of a microprocessor (not shown) for control purposes.

The defibrillator according to the invention further includes an impedance measurement circuit 8 which, after the pre-pulse 2, continuously measures the impedance situation between the defibrillation electrodes. The impedance measurement circuit 8 is also controlled by the microprocessor in the defibrillation circuit 6. Thus, the impedance measurement is started and stopped via a first port of the microprocessor, whereas a second port on the microprocessor reads the obtained and A/D-converted impedance signal.

Figure 3:
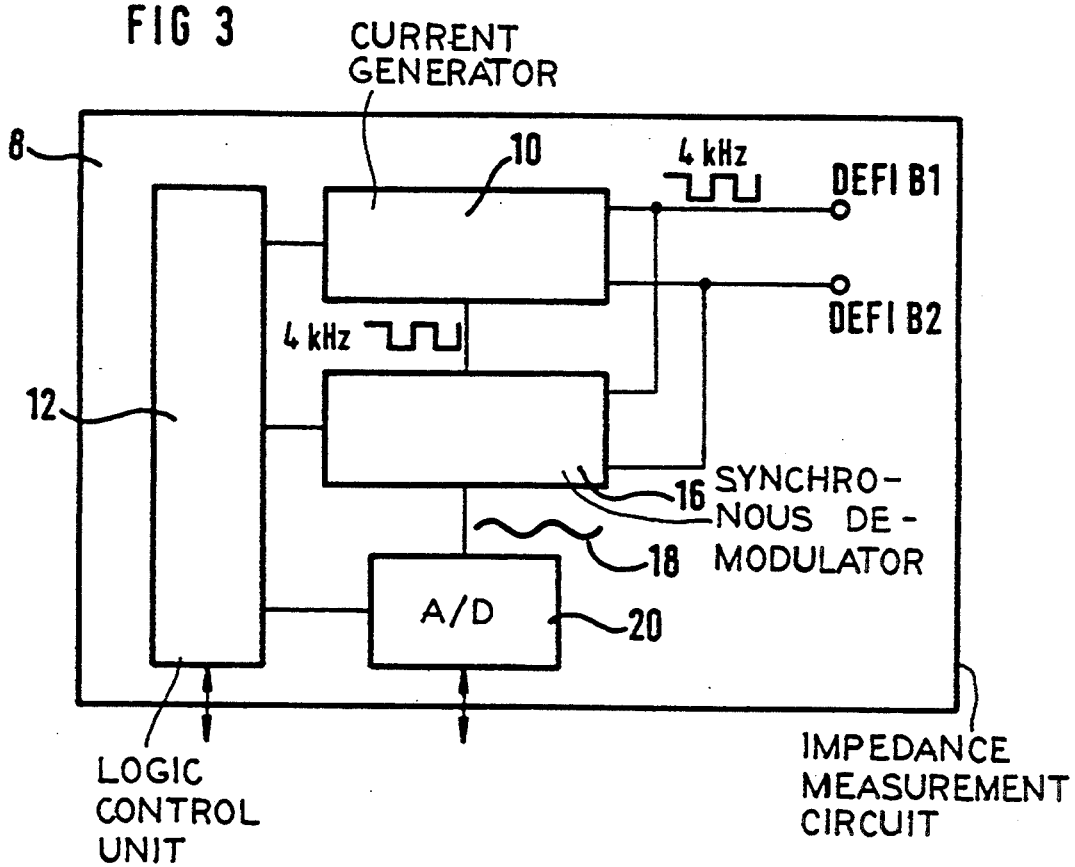
FIG. 3 shows a block diagram of the impedance measurement circuit for use in the heart defibrillator according to the invention.

The impedance measurement circuit 8 includes a current generator 10, which is caused, through a logic control unit 12, by the microprocessor in the defibrillation circuit to emit a measurement current with a frequency of 4 kHz (cf. FIG. 3). This measurement current is emitted across contacts DEFIB 1 and DEFIB 2 of the defibrillation electrodes.

A measurement signal, also with a measurement frequency of 4 kHz and with varying, impedance-dependent amplitude, is received, and a signal synchronous with the measurement current and the received measurement signal is sent to a synchronous demodulator 16. The output signal from this demodulator 16 consists of a low-frequency signal representing the impedance variation measured across contacts DEFIB 1 and DEFIB 2. This impedance signal is illustrated at 18 in FIG. 3.

The impedance signal 18 is fed to the A/D converter 20 and then sent to the microprocessor in the defibrillation circuit 6.

The A/D-converted signal is stored in the defibrillation circuit 6 and is analyzed by the microprocessor according to a special program for establishing the optimal time for emission of the defibrillation pulse 4.

Thus, the defibrillation pulse is emitted when a predesignated optimal impedance situation is detected.

Figure 4:
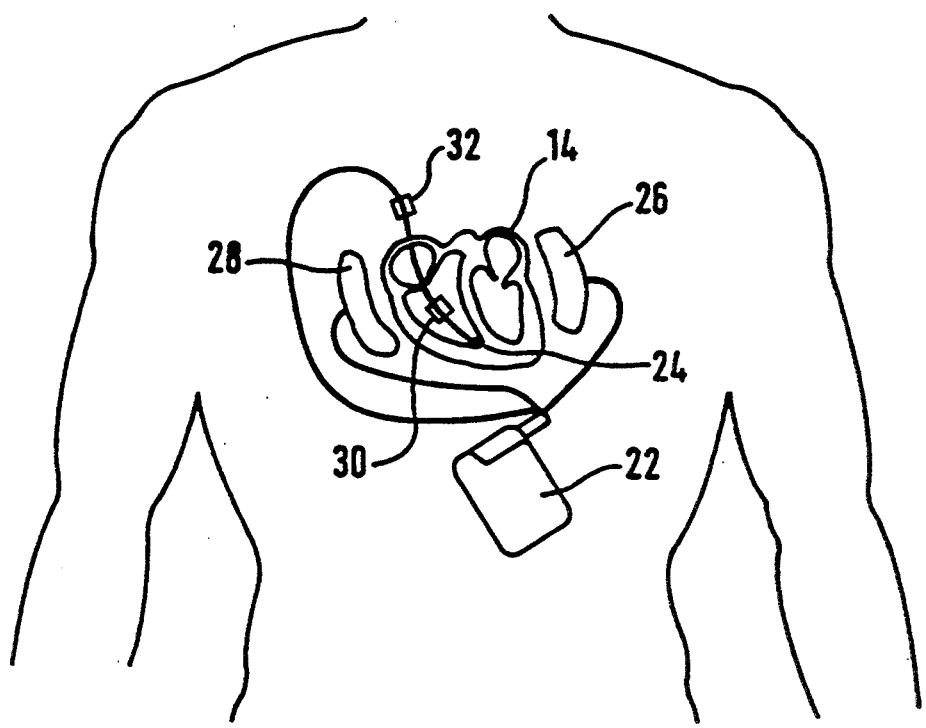
FIG. 4 shows a therapeutic device constructed in accordance with the principles of the present invention, implanted with a number of electrodes in and around the heart of a patient, for heart stimulation.

FIG. 4 schematically shows a plurality of different heart electrodes 22, 24, 26, 28, 30 and 32 arranged in and around the heart 14. The device case 22 can also serve as an electrode, with electrodes 26 and 28 being patch electrodes arranged on either side of the heart 14. The pre-pulse 2 and the defibrillation pulse 4 can be optionally emitted either by the same or different electrodes. Both the defibrillation electrodes and the time for the defibrillation pulse are selected so that current distribution and current density become optimal in the myocardium, so that the largest possible portion of the heart is subjected to the defibrillation shock.

One embodiment has been described above in which the time for emission of the defibrillation pulse is established by impedance monitoring, whereby the defibrillation pulse 4 is emitted when a designated, optimal impedance situation is detected between the defibrillation electrodes. The impedance normally drops after the pre-pulse 2, and the designated impedance situation for emission of the defibrillation pulse 4 can then be based on the drop in the impedance below a designated level. However, the defibrillator according to the invention can be devised so the defibrillation pulse 4 is emitted at a time, which can be a designated period of time, after the pre-pulse 2. The interval between the pre-pulse 2 and the defibrillation pulse 4 is then determined from practical experience. The time elapsing between the pre-pulse 2 and the defibrillation pulse 4 is normally less than 0.5 s.

The heart defibrillator according to the invention can further be devised as an implantable or external defibrillator.

Although modifications and changes may be suggested by those skilled in the art, it is the intention of the inventor to embody within the patent warranted hereon all changes and modifications as reasonably and properly come within the scope of his contribution to the art.

I claim as my invention:

1. A cardiac defibrillator comprising:
   pulse generator means for delivering electrical pulses in vivo to a heart via a plurality of electrodes, including at least one pulse having an intensity for effecting defibrillation of said heart;
   control means for controlling said pulse generator means for generating and delivering a pre-pulse via electrodes in said plurality of electrodes, prior to said pulse for effecting defibrillation, having lower intensity than said pulse for effecting defibrillation and of sufficient intensity for inducing mechanical contraction of muscles in the thorax;
   impedance measuring means for measuring an impedance situation, after delivery of said pre-pulse, between said electrodes in said plurality of electrodes via which said pre-pulse was delivered for identifying an optimum impedance situation for delivering said at least one pulse having an intensity for effecting defibrillation; and
   said control means comprising means for controlling said pulse generator means for delivering said at least one pulse having an intensity for effecting defibrillation of said heart at a predetermined time relative to when said optimum impedance situation measured by said impedance measuring means is present in said heart.

2. A defibrillator as claimed in claim 1 wherein said pulse generator means comprises means for delivering said at least one pulse for effecting defibrillation and said pre-pulse between the same electrodes of said plurality of electrodes.

3. A defibrillator as claimed in claim 1 wherein said pulse generator means includes a plurality of electrodes, and wherein said pulse generator means delivers said pulse for effecting defibrillation and said pre-pulse between different electrodes of said plurality of electrodes.

4. A defibrillator as claimed in claim 1 wherein said control means comprises means for operating said pulse generator means for emitting said pulse for effecting defibrillation within a maximum of 0.5 seconds after said pre-pulse.

5. A defibrillator as claimed in claim 1 wherein said impedance measurement means comprises:
   current generator means for delivering a measurement current to the heart via said electrodes in said plurality of electrodes via which said pre-pulse was delivered; and
   synchronous demodulator means for receiving a signal via said electrodes in said plurality of electrodes having a same phase as said measurement current and an amplitude dependent on the impedance between said electrodes in said plurality of electrodes.

6. A defibrillator as claimed in claim 5 wherein said control means is a digital control means, wherein said synchronous demodulator means comprises means for generating a low-frequency analog output signal representing a variation in the impedance between said electrodes in said plurality of electrodes, and wherein said impedance measurement means further comprises an analog-to-digital converter connected to said synchronous demodulator means for receiving said analog output signal therefrom, and converting said analog output signal into a corresponding digital signal for supply to said digital control means.

7. A defibrillator as claimed in claim 6 wherein said digital control means includes a microprocessor, said microprocessor including means for analyzing said signal from said analog-to-digital converter to identify said predetermined measured impedance situation.

8. A defibrillator as claimed in claim 1 wherein said control means comprises means for operating said at least one pulse generator means for emitting said pulse for affecting defibrillation when the impedance between said electrodes in said plurality of electrodes drops to a predetermined value.

9. A method for defibrillating a heart comprising the steps of:
   prior to delivery in vivo of a pulse to a heart for effecting defibrillation, delivering a pre-pulse to said heart having a lower intensity than said pulse for effecting defibrillation but with sufficient intensity for inducing mechanical contraction of muscles in the thorax;
   measuring the impedance of said heart after delivery of said pre-pulse to identify an optimum impedance situation for delivering said pulse for effecting defibrillation; and
   delivering said pulse for effecting defibrillation after said pre-pulse at a predetermined time relative to when said optimum impedance situation is measured in said heart.

10. A method as claimed in claim 9 comprising the additional step of: emitting said pulse for effecting defibrillation within a maximum of 0.5 seconds following said pre-pulse.

11. A method as claimed in claim 9 comprising the additional step of: delivering said pulse for effecting defibrillation following a predetermined time after said pre-pulse.

12. A method as claimed in claim 9 wherein the step of delivering said pulse for effecting defibrillation when said optimum impedance situation is present is further defined by delivering said pulse for effecting defibrillation when the impedance of said heart drops below a predetermined value.

* * * * *